(12) United States Patent
Dirix et al.

(10) Patent No.: US 9,447,061 B2
(45) Date of Patent: Sep. 20, 2016

(54) PROCESS FOR PREPARING EPICHLOROHYDRIN FROM DICHLOROHYDRIN

(71) Applicant: AKZO NOBEL CHEMICALS INTERNATIONAL B.V., Amersfoort (NL)

(72) Inventors: Carolina Anna Maria Christina Dirix, Diepenveen (NL); André Michiel Koolaard, Zwolle (NL); Antoon Jacob Berend Ten Kate, Arnhem (NL); Eilertdina Henderika Renkema, Renkum (NL)

(73) Assignee: Akzo Nobel Chemicals International B.V., Amersfoort (NL)

( * ) Notice: Subject to any disclaimer, the term of this patent is extended or adjusted under 35 U.S.C. 154(b) by 0 days.

(21) Appl. No.: 14/432,996

(22) PCT Filed: Oct. 23, 2013

(86) PCT No.: PCT/EP2013/072110
§ 371 (c)(1),
(2) Date: Apr. 1, 2015

(87) PCT Pub. No.: WO2014/064127
PCT Pub. Date: May 1, 2014

(65) Prior Publication Data
US 2015/0274684 A1    Oct. 1, 2015

Related U.S. Application Data

(60) Provisional application No. 61/721,643, filed on Nov. 2, 2012.

(30) Foreign Application Priority Data

Oct. 26, 2012 (EP) .................................. 12190182

(51) Int. Cl.
*C07D 301/27* (2006.01)
*C07D 301/26* (2006.01)
(Continued)

(52) U.S. Cl.
CPC ........... *C07D 301/26* (2013.01); *C07D 301/24* (2013.01); *C07D 301/32* (2013.01)

(58) Field of Classification Search
CPC . C07D 301/26; C07D 301/24; C07D 301/32
USPC ........................................................ 549/514
See application file for complete search history.

(56) References Cited

U.S. PATENT DOCUMENTS

2013/0225843 A1* 8/2013 Krafft ..................... C07C 29/62
549/518

FOREIGN PATENT DOCUMENTS

GB     2173496 A  *  4/1985
JP     2009 184943    8/2009
(Continued)

OTHER PUBLICATIONS

International Search Report and Written Opinion for Application No. PCT/EP2013/072110, mailed on Nov. 14, 2013.
(Continued)

*Primary Examiner* — T. Victor Oh
(74) *Attorney, Agent, or Firm* — McDonnell Boehnen Hulbert & Berghoff LLP

(57) ABSTRACT

The present invention pertains to a process for preparing a product rich in epichlorohydrin, comprising the steps of: a) reacting a mixture of dichlorohydrin and a base at a temperature in the range of 0-40° C. during a period of time in the range from 1 second to 180 minutes, wherein the base is present in a less than stoichiometric amount, to obtain a reaction mixture comprising epichlorohydrin and brine; b) subjecting at least part of the reaction mixture to a separation step to form a product fraction which is rich in epichlorohydrin and a brine fraction which is lean in epichlorohydrin; c) subjecting at least part of the brine fraction to a purification step to yield a purified brine. It has been found that the process according to the invention allows the manufacture of epichlorohydrin from dichlorohydrin on an industrial scale at high yield, while at the same time providing a brine with a low total organic carbon content without extensive separation being necessary.

19 Claims, 1 Drawing Sheet

Figure 1:
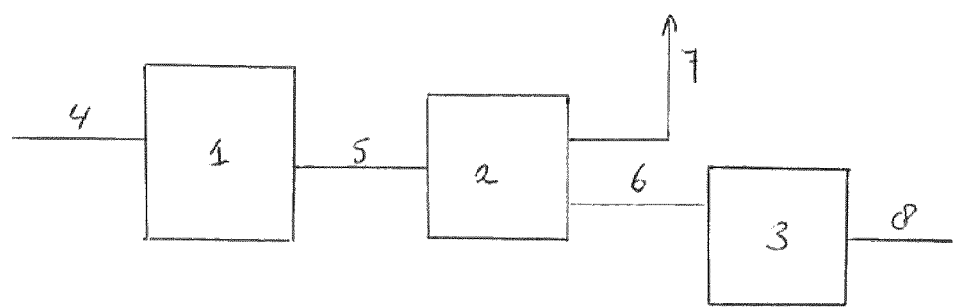

(51) Int. Cl.
*C07D 301/24* (2006.01)
*C07D 301/32* (2006.01)

(56) References Cited

FOREIGN PATENT DOCUMENTS

| WO | WO 95/14635 | 6/1995 | | |
|---|---|---|---|---|
| WO | WO 2008/101866 | 8/2008 | | |
| WO | WO 2009/026208 | 2/2009 | | |
| WO | WO 2009/026209 | 2/2009 | | |
| WO | WO2011092270 | * | 8/2011 | |

OTHER PUBLICATIONS

Braun, Geza; Epichlorohydrin and Epibromohydrin, Organic Synthesis, Coll. vol. 2, p. 256; vol. 16, p. 30, 2002.
Clarke, H.T., et al., Epichlorohydrin, Orgainic Synthesis, Coll. vol. 1, p. 233; vol. 3, p. 47, 2002.

* cited by examiner

PROCESS FOR PREPARING EPICHLOROHYDRIN FROM DICHLOROHYDRIN

REFERENCE TO RELATED APPLICATIONS

This application is the U.S. National Phase of PCT/EP2013/072110, filed on Oct. 23, 2013, and claims the benefit of EP Application No. 12190182.1, filed on Oct. 26, 2012, and U.S. Provisional Application No. 61/721,643, filed on Nov. 2, 2012.

The present invention relates to a process for preparing epichlorohydrin from dichlorohydrin. More in particular, the invention relates to a process for preparing epichlorohydrin from dichlorohydrin and a base at low temperatures.

Epichlorohydrin is an intermediate in the manufacture of many industrial products, e.g., epoxyresins, elastomers, and polyamide resins.

Processes for the preparation of epichlorohydrin from dichlorohydrin and a base at low temperatures are known in the art. For example, *Organic Synthesis, Coll.* Vol. 2, p. 256, Vol. 16, p. 30 and *Organic Synthesis, Coll.* Vol. 1, p. 233, Vol 3, p. 47 disclose process embodiments for the preparation of epichlorohydrin from dichlorohydrin by reaction with an inorganic base such as NaOH or $Ca(OH)_2$ at low temperatures, whereupon the formed epichlorohydrin is recovered from the initial reaction mixture by distillation. These references describe the process on a laboratory scale.

A side product of this process is a substantial brine fraction which contains the chlorine removed from the dichlorohydrin and the cation remaining from the base. When the process is carried out on an industrial scale, this substantial brine fraction needs to be processed further. While there are numerous ways to process brine fractions, it has been found that they all require the brine to be relatively free of organic components, as is evidenced from a low total carbon content. A particularly attractive way to process a brine fraction is by subjecting it to membrane electrolysis, but especially for this process a very low carbon content is required, namely below 20 mg/kg, in particular below 10 mg/kg. It has been found that the provision of a brine fraction as side product from the epichlorohydrin manufacture with a carbon content in this range is difficult, and often requires extensive, and thus costly processing.

Therefore, it would be desirable to have an improved process for the preparation of epichlorohydrin from dichlorohydrin and a base which does not have the above-mentioned disadvantages and which would provide epichlorohydrin at lower production costs accompanied by a relatively pure brine fraction. An object of the present invention is to provide such a desired improved process.

As a result of extensive research and experimentation such an improved process has now surprisingly been found.

Accordingly, the present invention relates to a process for preparing a product rich in epichlorohydrin, comprising the steps of:
a) reacting a mixture of dichlorohydrin and a base at a temperature in the range of 0-40° C. during a period of time in the range from 1 second to 180 minutes, wherein the base is present in a less than stoichiometric amount, to obtain a reaction mixture comprising epichlorohydrin and brine;
b) subjecting at least part of the reaction mixture to a separation step to form a product fraction which is rich in epichlorohydrin and a brine fraction which is lean in epichlorohydrin;
c) subjecting at least part of the brine fraction to a purification step to yield a purified brine.

It has been found that the process according to the invention allows the manufacture of epichlorohydrin from dichlorohydrin on an industrial scale at high yield, while at the same time providing a brine with a low total organic carbon content without extensive separation being necessary. Further objects and advantages of the present invention will become clear from the further specification.

The process according to the invention is carried out on an industrial scale. In one embodiment, the volume flow of the reaction mixture comprising epichlorohydrin and brine to the separation step is at least 0.25 $m^3$/h, in particular at least 1 $m^3$/h.

A first important characterizing feature in the present process is formed by a combination of low reaction temperatures and, preferably, short residence times. As generally recognized, while a low temperature will normally result in a low reaction rate, by using very large reactors the required productivity can still be reached. This, however, requires large capital investments, which is undesired. Therefore, a person skilled in the art would be primarily led away from such low temperatures when in charge of providing the desired improved process. It has been found, however, that the selection of a reaction temperature in the specified range is required to obtain the effect of the invention, and that the processing is further improved by the selection of short reaction times, as will be elucidated below.

The temperature in reaction step (a) of the present process is at most 40° C. It has been found that at higher temperatures the effect of the present invention will not be obtained. It should be noted that it may be necessary to apply cooling to the reaction system to keep the temperature within the required ranges. This may be of particular relevancy where the dichlorohydrin contains HCl as contaminant product, as the reaction between HCl and base is highly exothermic. In particular embodiments of the invention, the temperature is at most 35° C., in particular at most 30° C., more in particular at most 28° C., preferably at most 25° C., more preferably at most 23° C. On the other hand, the lower limit for the temperature in step (a) is not critical. In general, it is at least 0° C., preferably at least 10° C., and more preferably at least 15° C. According to a preferred embodiment, the temperature due in reaction step (a) is in the range of 10-28° C., more preferably in the range of 15-23° C.

A further important characterizing feature in the present process is the use of a less than stoichiometric amount of base. This means that full conversion of the dichlorohydrin to epichlorohydrin cannot be attained. This is of course counterintuitive to the skilled person seeking to manufacture epichlorohydrin from dichlorohydrin. It has been found, however, that the use of a less than stoichiometric amount of base is required to obtain the effect of the invention. In one embodiment, an amount of base is applied which is at most 99.5% of the stoichiometric amount, in particular at most 99.0%, more in particular at most 98.5%, still more in particular at most 97.5%. While this may appear to be only marginally less than stoichiometric, it has been found that these values are important to obtain the effect of the present invention.

In one embodiment, an amount of base is applied which is at least 50% of the stoichiometric amount, in particular at least 60%, more in particular at least 70%, still more in particular at least 80%, taking the above maximum values into account. It may be advantageous to use a relatively large amount of base, e.g., at least 90% of the stoichiometric amount, in particular at least 93%, taking the above maximum values into account.

The reaction in step (a) is generally carried out at a pH in the range of 7-16. According to a preferred embodiment of this invention, the reaction (a) in the process is carried out at a pH of at most 15.5, more preferably at most 15. Preferably, the pH during said reaction step (a) is at least 8. The pH during said reaction step (a) is preferably in the range of 8-16, more preferably in the range of 8-15.5, and most preferably in the range of 8-15.

In the reaction step (a) of the present invention the period of time for reacting the dichlorohydrin, also indicated as the residence time, may vary from 1 second to 180 minutes. Preferably, this residence time is at least 5 seconds and most preferably at least 15 seconds. On the other hand the residence time in reaction step (a) is preferably at most 60 minutes, and more preferably at most 30 minutes. According to a preferred embodiment of the present invention, the residence time is in the range of 5 seconds to 60 minutes, and more preferably in the range of 15 seconds to 30 minutes.

If reaction/residence periods are used which are relatively long within the ranges indicated above, it is considered preferred to combine them with temperatures which are relatively low within the ranges indicated above. In one embodiment where a reaction temperature of more than 30° C. is used, a reaction time below 10 minutes is preferably used, more preferably below 5 minutes. In another embodiment where a reaction temperature in the range of 15-25° C. is used, it may be preferred to use a reaction time of 15-60 minutes, in particular 20-40 minutes. Lower temperatures will generally require a longer reaction time.

It is preferred that the separation step is started as soon as possible following the reaction step. Therefore, preferably, the reaction mixture withdrawn from the reactor is provided directly to the separation step. In one embodiment, the residence time in the connection lines and, where present, buffer vessels between the reaction unit and the separation unit is at most 180 minutes, preferably at most 60 minutes, more preferably at most 15 minutes, and in one embodiment at most 10 minutes.

The pressure in the reaction step is not critical to the present invention. In one embodiment, the reaction is carried out at a pressure in the range of 0.1-10 bar. Atmospheric pressure is suitable.

In one embodiment, the reaction step (a) is carried out under mixing conditions, in particular using mechanical stirring or static mixing.

It will be appreciated that the starting dichlorohydrin may be 1,2-dichlorohydrin, 1,3-dichlorohydrin, or mixtures thereof. Preferably, dichlorohydrin is used which consists for at least 50% of 1,3-dichlorohydrin, in particular at least 70%, more in particular at least 80%.

The applied base can be selected from a variety of inorganic or organic bases. Preferably, said base will be selected from the group consisting of alkali metal hydroxides and alkaline metal hydroxides. More preferably, sodium hydroxide and/or or calcium hydroxide are used. In one embodiment, the base is dissolved or suspended in an aqueous medium.

Where the base is dissolved in an aqueous medium, its concentration is governed by various parameters. If the concentration is low, a large amount of water is added to the system without generating benefit. On the other hand, it is preferred for the amount of water present in the system to be such that the brine fraction produced after the distillation step is at or below its saturation concentration. In this it should be taken into account that some water may end up in the epichlorohydrin product fraction, and that side reactions may generate or consume water. In one embodiment, the base is NaOH provided in an aqueous solution with a concentration of 10-25 wt. %, in particular 15-20 wt. %. It is within the scope of the skilled person to determine a suitable base concentration.

When the desired reaction time or residence time has passed, at least part of the reaction mixture is subjected to a separation step (b) to form a product fraction which is rich in epichlorohydrin and a brine fraction which is lean in epichlorohydrin. For best processing efficiency it is preferred to provide the entire reaction mixture as obtained in step (a) to separation step (b).

The reaction mixture that is subjected to the separation step comprises an organic fraction and an aqueous fraction. The organic fraction, which is defined as the total amount of organic compounds, can, e.g., make up between 5 and 50 wt. % of the total reaction mixture, in particular between 10 and 45 wt. %, more in particular between 15 and 40 wt. %. The exact content will depend on the nature of the base and the amount of water in the system, as will be evident to the skilled person. The aqueous fraction is defined as the reaction mixture minus the organic fraction, i.e. the total amount of water, base and salt, which can, e.g., make up between 50 and 95 wt. % of the total reaction mixture. The organic fraction generally comprises at least 85 wt. % of epichlorohydrin, preferably at least 90 wt. %, more preferably at least 95 wt. %, calculated on the total amount of organic compounds.

The organic fraction generally comprises at most 15 wt. % of dichlorohydrin, preferably at most 10 wt. %, more preferably at most 5 wt. %, calculated on the total amount of organic compounds.

The organic fraction may contain contaminants, in particular glycidol and glycerol. It is preferred for the amount of contaminants to be as low as possible. Therefore, the organic fraction generally comprises at most 1 wt. % of glycidol, preferably at most 0.5 wt. %, more preferably at most 0.2 wt. %, calculated on the total amount of organic compounds.

The organic fraction generally comprises at most 0.2 wt. % of glycerol, preferably at most 0.1 wt. %, more preferably at most 0.01 wt. %, calculated on the total amount of organic compounds. It is a particular feature of the present invention, due to the particular selection of reaction temperature and amount of base, that the glycerol concentration in the reaction mixture is very low indeed. Not wishing to be bound by theory, it is believed that this feature is in part responsible for the fact that in the process according to the invention a brine fraction with a very low carbon content may be obtained.

The reaction mixture may show liquid-liquid phase separation. As indicated above, for best processing efficiency it is preferred to provide the entire reaction mixture as obtained in step (a) to separation step (b).

The separation step (b) may be carried out in various manners. The separation step (b) results in the formation of an epichlorohydrin-rich fraction and an epichlorohydrin-lean brine fraction, wherein the concentration of epichlorohydrin in the epichlorohydrin-rich fraction is higher than the concentration of epichlorohydrin in the epichlorohydrin-lean brine fraction.

In a first embodiment, the separation step is a distillation step that is carried out under subatmospheric conditions. In the distillation step the product epichlorohydrin is removed over the top of the distillation. The bottom fraction is the brine fraction. Subatmospheric conditions are used to keep the temperature in the column in a reasonable range, while at the same time ensuring adequate distillation efficiency. In one embodiment, the pressure is selected to be below 500 mbar. In one embodiment, the pressure is in the range of 100-300 mbar. This allows the performance of the distillation step at acceptable temperatures in commercially available apparatus.

In one embodiment of the present invention, reaction step (a) and distillation step (b) are combined and the pressure is selected such that the temperature of the bottom fraction in the distillation column is at most 40° C., in particular at most 35° C., more in particular at most 28° C., preferably at most 25° C., more preferably at most 23° C.

In one embodiment, the separation step encompasses a liquid-liquid separation step followed by a distillation step. This embodiment has the advantage that the volume to be provided to the distillation step is reduced, resulting in substantial energy savings. Further, due to the relatively mild conditions prevailing during the liquid-liquid separation step, the formation of byproducts is reduced. Further, the relatively mild conditions place less stringent requirements on the properties of the apparatus, allowing the use of more economic process design.

In this embodiment at least part of the reaction mixture as obtained in step (a) is introduced into a liquid-liquid separator wherein the mixture is separated into a first product which is rich in epichlorohydrin and a second product which is lean in epichlorohydrin. For reasons of process efficiency it may be preferred for the entire epichlorohydrin-containing reaction mixture as obtained in step (a) to be introduced into the liquid-liquid separator in step (b).

The liquid-liquid separation step is preferably carried out at a temperature of at most 65° C., preferably at most 55° C., more preferably at most 45° C., and most preferably at most 35° C. On the other hand, this step is preferably carried out at a temperature of at least 0° C., preferably at least 10° C., and more preferably at least 20° C. In a preferred embodiment the temperature in the liquid-liquid separation step is in the range of 0-65° C., more preferably in the range of 10-55° C., even more preferably in the range of 20-45° C., and most preferably in the range of 20-35° C.

The residence time in the liquid-liquid separation step preferably is at least 1 minute, more preferably at least 5 minutes. On the other hand, the residence time in the liquid-liquid separation step preferably is at most 240 minutes, preferably at most 30 minutes. According to a preferred embodiment of this step, the residence time is in the range of 1-240 minutes, more preferably in the range of 1-120 minutes, and most preferably in the range of 5-30 minutes.

If so desired, a solvent may be added to the reaction mixture obtained in step (a) before or during the liquid-liquid separation step, in order to reach an improved separation efficiency. If so desired, a solvent may even be present during the reaction step, as long as it does not interfere with the reaction. If a solvent is present during the liquid separation step, it is preferably added after the reaction step is completed and before the liquid-liquid separation is started. Suitable solvents are immiscible with water. Preferably, they have a boiling point below 100° C. Suitably, an organic solvent can be used, e.g., a solvent selected from the group of n-butylchloride, 3-methylhexane, 2-methylhexane, 3-ethylpentane, diisopropyl-ether, 2,2,3-trimethylbutane, 1,1-dichloropropane, 1,1,1-trichloroethane. The solvent, if used, preferably is inert with regard to the components of the reaction mixture under reaction conditions.

Suitable liquid-liquid separators are known in the art, and can be selected from a great variety of commercially available industrial equipment. Tank separators or centrifuges may be mentioned as examples. Other suitable equipment will be clear to the skilled person.

The liquid-liquid separation step results in the formation of an epichlorohydrin-rich fraction and an epichlorohydrin-lean brine fraction, wherein the concentration of epichlorohydrin in the epichlorohydrin-rich fraction is higher than the concentration of epichlorohydrin in the epichlorohydrin-lean brine fraction.

The epichlorohydrin-lean brine fraction obtained from the liquid-liquid separation step is subjected to a reduced pressure-distillation step, as described above, to again form an epichlorohydrin-rich product fraction and an epichlorohydrin-lean brine fraction. For a description of the reduced pressure-distillation step reference is made to what is stated above.

The separation step (b) yields an epichlorohydrin-rich product fraction and an epichlorohydrin-lean brine fraction.

The epichlorohydrin-rich product fraction consists of an organic fraction and a water fraction. In general, the epichlorohydrin-rich product fraction comprises 10-90 wt. % of organic fraction and 90-10 wt. % of water. Preferably, the epichlorohydrin-rich product fraction comprises at least 20 wt. % of organic compounds, more preferably at least 40 wt. %.

The organic fraction of the epichlorohydrin-rich product fraction generally comprises at least 85 wt. % of epichlorohydrin, preferably at least 90 wt. %, more preferably at least 95 wt. %. The organic fraction of the epichlorohydrin-rich product fraction generally comprises at most 15 wt. % of dichlorohydrin, preferably at most 10 wt. %, more preferably at most 5 wt. %. Preferably, the organic fraction of the epichlorohydrin-rich product fraction contains less than 1 wt. % of the total of glycidol and glycerol, preferably less than 0.5 wt. %, more preferably less than 0.1 wt. %.

The epichlorohydrin-lean brine fraction generally comprises water, a salt, and a small amount of organic compound, in particular less than 1 wt. %. Preferably, the amount of organic compound in the epichlorohydrin-lean brine fraction is less than 0.5 wt. %. The amount of epichlorohydrin in the epichlorohydrin-lean brine fraction preferably is below 2,000 ppm, more preferably below 1,000 ppm. The amount of dichlorohydrin in the epichlorohydrin-lean preferably is below 4,000 ppm, more preferably below 2,000 ppm. The amount of glycidol preferably is below 2,000 ppm, more preferably below 1,000 ppm. The amount of the glycerol preferably is below 200 ppm, more preferably below 100 ppm. The amount of monochlorohydrin preferably is below 2,000 ppm, more preferably below 1,000 ppm.

The salt content of the epichlorohydrin-lean brine fraction will depend on the amount of water and base added to the system. The salt is a chloride salt, with the nature of the cation depending on the nature of the cation in the base. It is preferred for the amount of chloride salt to be at or below the saturation value of the solution. For example, where the salt is NaCl, the brine preferably contains between 100 and 320 g/liter.

At least part, and preferably all, of the epichlorohydrin-lean brine fraction resulting from separation step (b) is subjected to a purification step (c) to remove organic compounds and yield a purified brine. The brine obtained in this step has a total organic carbon content of below 50 mg/kg, in particular below 20 mg/kg, preferably below 10 mg/kg, in some embodiments below 5 mg/kg. It has been found that the combination of the relatively low reaction temperature and a less than stoichiometric amount of base in step (a) in combination with the separation step (b) results in a brine faction which can be purified relatively easily to form a brine fraction with said low total organic carbon content. Although the purification step (c) may be carried out in more than one sequential step, it is preferred for the purification step (c) to encompass a single purification step. In one embodiment, the purification step (c) comprises, preferably consists of, an adsorption step, wherein the brine fraction obtained from separation step (b) is contacted with an adsorbent, wherein the adsorbent adsorbs organic molecules from the brine fraction. Suitable adsorbent materials comprise cationic clays, molecular sieves such as ZSM-5, and activated carbon. The use of activated carbon and molecular sieves, in particular zeolites, is particularly preferred, as it has been found to yield a product brine with a particularly low total organic carbon content. Activated carbon and molecular sieves are commercially available. Suitable types include Norit ROX, Norit SX-1 G, Zeolite ZSM, Lewatit VP, Zeolite EZ07.

Other purification methods may also be used in purification step (c). Examples include oxidation of organic compounds, e.g., using hypochlorite, ozone, or peroxides, alone or in combination, where the combination of ozone and peroxide may be mentioned especially, treatment with Fenton's reagent (peroxide+Fe(II) catalyst), extraction with organic solvents, crystallization, electrochemical processes, and biological treatments.

The process according to the invention may be carried out in batch, semi-batch, or continuous mode. In one embodiment, at least steps (a) and (b) are carried out in a semi-batch or a continuous mode of operation. More preferably, the process of steps (a) and (b), and in particular also encompassing step (c) is carried out in a continuous mode of operation.

In the above, the reaction step (a), the separation step (b), and the purification step (c) have been described as separate steps. It is possible, however, to perform two or more of these steps in an integrated fashion. For example, in one embodiment, the reaction step (a) and the separation step (b) are combined to form a reactive distillation step. In this embodiment care should be taken to ensure that the ratio between dichlorohydrin and base is within the stipulated range. Further, care should be taken to ensure that the reaction temperature is in the stipulated range.

Figure 2:
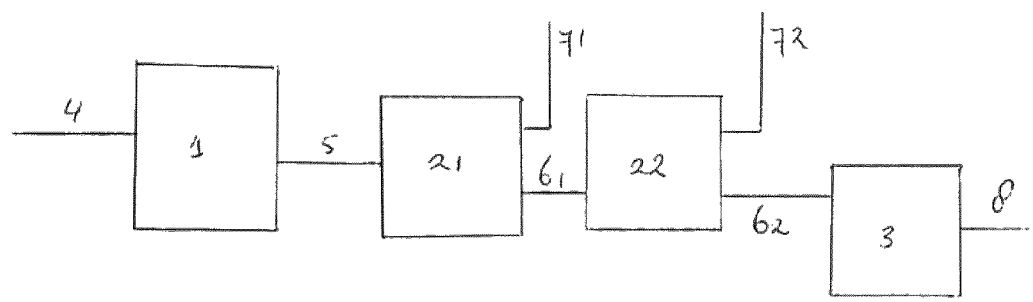

The present invention is illustrated by FIGS. 1 and 2, without being limited thereto or thereby.

In FIG. 1, dichlorohydrin and base are provided through feed input (4) to reactor (1). The feed input (4) can be a single stream or multiple streams, as will be evident to the skilled person. Reactor (1) can be a conventional reactor, preferably equipped with stirring means, such as a stirred tank reactor or a static mixer. In the reactor, reaction takes place and when the reaction is completed, reaction mixture is withdrawn from reactor (1) through line (5), and at least part, and preferably all, of the reaction mixture is provided to separation unit (2), which is, e.g., a distillation unit. In the distillation unit, distillation is effected, yielding an epichlorohydrin-rich fraction which is withdrawn from the top of the distillation unit through line (7), and a brine fraction which is withdrawn from the bottom of the distillation unit through line (6). At least part, and preferably all, of the brine fraction is provided to a brine purification unit (3), where it is purified to reduce the level of organic compounds, e.g., through adsorption. The purified brine thus formed is withdrawn through line (8).

In FIG. 2, a variation on the above process is presented. Dichlorohydrin and base are provided through feed input (4) to reactor (1). Reaction mixture is withdrawn from reactor (1) through line (5), and at least part of the reaction mixture is provided to liquid-liquid separation unit (21). From the liquid-liquid separation unit (21) an epichlorohydrin-rich stream is withdrawn through line (71). The brine fraction, which still contains epichlorohydrin, is withdrawn from the liquid-liquid separation unit (21) through line (61) and provided to distillation unit (22). From the top of distillation unit (22) an epichlorohydrin-rich fraction is obtained through line (72) and a brine fraction is withdrawn from the bottom of the distillation unit through line (62). At least part, and preferably all, of the brine fraction is provided to a brine purification unit (3) to form a purified brine, which is withdrawn through line (8).

The present invention is elucidated by the following examples, without being limited thereto or thereby.

EXAMPLE 1 ACCORDING TO THE INVENTION

Step (a)—Reaction Step

A batch reactor consisting of a double-wall vessel of 4 liters equipped with four baffles, a Klöpper bottom, an outlet valve at the bottom, and a stirrer (blades positioned to obtain upward fluid movement) was provided with 1,064 g 1,3-dichloro-2-propanol (8.25 mol) obtained from Acros Organics (Geel, Belgium). Subsequently, 1,752 g 18% w/w sodium hydroxide (7.9. mol) were added. The 18 wt. % sodium hydroxide solution was prepared by diluting 50 wt. % sodium hydroxide obtained from Sigma-Aldrich Chemie B.V. (Zwijndrecht, the Netherlands). The contents of the reactor were cooled and kept at atmospheric pressure. Due to excess 1,3-dichloro-2-propanol, the theoretical conversion was limited to 96%. After the addition of sodium hydroxide, the stirrer was started (200 rpm) and the pH, the temperature, and the stirrer speed were monitored during the reaction that was continued for 25 minutes. The temperature remained at 16.4±0.8° C. throughout the reaction. After 25 minutes the stirrer was stopped and liquid-liquid phase separation took place. The reaction product consisted of an organic phase and an aqueous phase. Samples were taken from each phase to determine the composition of both the organic phase and the aqueous phase. The results are presented in Table 1. The overall conversion to epichlorohydrin was 93.5%.

Step (b)—Separation Step

The entire product of the reaction step, encompassing both the organic phase and the aqueous phase, was subjected to a separation step as follows: The feed vessel of the distillation column was filled with 2,750 g of the product. Stirring was used to obtain a well mixed feed. The feed was pumped into the distillation column and introduced at the upper stage of the column. The distillation column was a thermally insulated column with 10 stages equipped with inverted cups. The distillation was performed at 200 mbar. An epichlorohydrin-lean brine fraction was obtained from the reboiler outlet and the epichlorohydrin-rich product fraction was condensed with an intensive cooler. Samples were taken from the bottom section (reboiler) and from the distilled product. The distilled product again consisted of two phases, an organic phase and a water phase. The composition was determined for all phases (see Table 1).

TABLE 1

Composition of various fractions

|  | 1,3-dichloro-2-propanol [wt. %] | 2,3-dichloro-2-propanol [wt. %] | epichlorohydrin [wt. %] | glycerol [wt. %] | glycidol [wt. %] | Water/brine [wt. %] |
| --- | --- | --- | --- | --- | --- | --- |
| Dichlorohydrin starting material | 99.8 | 0.2 | — | — | — | — |
| Product of step (a)—organic phase | 5.7 | 0.7 | 92.2 | <0.01 | 0.02 | 1.4 |
| Product of step (a)—aqueous phase | 0.24 | 0.02 | 2.22 | <0.01 | 0.03 | 97.6 |
| Product of step (b)—product fraction—organic phase | 5.6 | 0.7 | 91.9 | <0.01 | <0.01 | 1.9 |
| Product of step (b)—product fraction—water phase | 0.77 | 0.07 | 5.97 | <0.01 | 0.02 | 93.2 |
| Product of step (b) brine fraction | <0.01 | 0.01 | <0.01 | <0.01 | 0.03 | 100 |

As can be seen from Table 1, the brine product from separation step (b) has a organic content of 0.03 wt. % glycidol and 0.01 wt. % dichlorohydrin. This brine can be further purified in one purification step (c).

Step (c) Purification Step

The brine fraction of step (b) was provided as feed to a purification step by contacting it with active carbon Norit ROX 0.8 granular in an amount of 10 grams of carbon per 100 grams of brine fraction. The mixture was shaken overnight at room temperature. The concentration of the organic components in the feed and in the purified brine product is given in Table 2. The organic content is defined as TOO (total organic carbon in mg C/kg).

TABLE 2

Organic component content in the brine fraction before and after purification

|  | Concentration feed wt. % | TOC feed measured mg C/kg | TOC purified brine mg C/kg |
| --- | --- | --- | --- |
| Brine product of separation step (b) | 0.03 + 0.01 | 179 | 5 |
| Glycidol + Dichlorohydrin | | | |

As can be seen from Table 2, the final brine product from purification step (c) has a total organic carbon content (TOC) of 5 mg C/kg. A brine fraction with this low carbon content can be processed in many ways, including by provision to electrodialysis units.

COMPARATIVE EXAMPLE A

Example 1 was repeated, except that in step a) the temperature was raised to 32° C. However the reaction time was maintained at 25 minutes. All other steps were carried out in the same manner. Table 3 below provides the composition of the various fractions.

TABLE 3

Composition of various fractions

|  | 1,3-dichloro-2-propanol [wt. %] | 2,3-dichloro-2-propanol [wt. %] | epichlorohydrin [wt. %] | glycerol [wt. %] | glycidol [wt. %] | Water/brine [wt. %] |
| --- | --- | --- | --- | --- | --- | --- |
| Dichlorohydrin starting material | 99.8 | 0.2 | — | — | — | — |
| Product of step (a)—organic phase | 6.1 | 0.7 | 91.6 | <0.01 | 0.17 | 1.5 |
| Product of step (a)—aqueous phase | 0.21 | 0.02 | 2.1 | 0.01 | 0.63 | 97.0 |
| Product of step (b)—product fraction—organ phase | 5.9 | 0.7 | 91.5 | <0.01 | 0.01 | 1.8 |
| Product of step (b)—product fraction—water phase | 0.85 | 0.06 | 5.7 | <0.01 | 0.03 | 93.4 |
| Product of step (b) brine fraction | <0.01 | 0.01 | <0.01 | 0.01 | 0.68 | 99.3 |

As can be seen from Table 3, the brine product from separation step (b) now has a organic content of 0.68 wt. % of glycidol and 0.01 wt. % of glycerol. When this brine was subjected to purification step (c) carried out as described above, a total organic carbon content (TOC) of 77 mg C/kg was obtained. A brine fraction with this carbon content is not suitable for direct further processing, and requires additional purification.

The invention claimed is:

1. A process for preparing a product rich in epichlorohydrin, comprising the steps of:
   a) reacting a mixture of dichlorohydrin and a base at a temperature in the range of 0-40° C. during a period of time in the range from 1 second to 180 minutes, wherein the base is present in an amount of at most 99.0% of the stoichiometric amount, to obtain a reaction mixture comprising epichlorohydrin and brine;
   b) subjecting at least part of the reaction mixture to a separation step to form a product fraction which is rich in epichlorohydrin and a brine fraction which is lean in epichlorohydrin;
   c) subjecting at least part of the brine fraction to a purification step to yield a purified brine.

2. The process according to claim 1, wherein the temperature of the reaction mixture in step (a) is at most 30° C.

3. The process according to claim 1, wherein the separation step (b) is a subatmospheric distillation step.

4. The process according to claim 1, wherein the separation step (b) comprises a liquid-liquid separation step followed by a subatmospheric distillation step.

5. The process according to claim 4, wherein the liquid-liquid separation step is carried out at a temperature of at most 65° C.

6. The process according to claim 3, wherein the subatmospheric distillation step is carried out at a pressure of below 500 mbar.

7. The process according to claim 3, wherein the reaction and separation are combined into a reactive distillation step in which the pressure is selected such that the temperature of the bottom fraction is at most 30° C.

8. The process according to claim 1, wherein the purification step consists of a single purification step.

9. The process according to claim 1, wherein the purification step comprises an adsorption step wherein the brine fraction is contacted with an adsorbent for organic molecules.

10. The process according to claim 9, wherein the adsorbent is active carbon or a molecular sieve.

11. The process according to claim 1, wherein the temperature of the reaction mixture in step (a) is at most 23° C.

12. The process according to claim 1, wherein in step (a) the base is present in an amount of at most 97.5% of the stoichiometric amount.

13. The process according to claim 11, wherein the separation step (b) is a subatmospheric distillation step.

14. The process according to claim 12, wherein the separation step (b) comprises a liquid-liquid separation step followed by a subatmospheric distillation step.

15. The process according to claim 4, wherein the liquid-liquid separation step is carried out at a temperature of at most 35° C.

16. The process according to claim 3, wherein the subatmospheric distillation step is carried out at a pressure in the range of 100-300 mbar.

17. The process according to claim 3, wherein the reaction and separation are combined into a reactive distillation step in which the pressure is selected such that the temperature of the bottom fraction is at most 23° C.

18. The process according to claim 4, wherein the purification step comprises an adsorption step wherein the brine fraction is contacted with an adsorbent for organic molecules.

19. The process according to claim 18, wherein the adsorbent is active carbon or a molecular sieve.

* * * * *